(12) United States Patent
Korporaal et al.

(10) Patent No.: US 9,999,401 B2
(45) Date of Patent: Jun. 19, 2018

(54) DETERMINING THE VELOCITY OF A FLUID WITH THE AID OF AN IMAGING METHOD

(71) Applicant: Siemens Aktiengesellschaft, München (DE)

(72) Inventors: Johannes Georg Korporaal, Forchheim (DE); Rainer Raupach, Heroldsbach (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 24 days.

(21) Appl. No.: 15/045,346

(22) Filed: Feb. 17, 2016

(65) Prior Publication Data

US 2016/0249874 A1 Sep. 1, 2016

(30) Foreign Application Priority Data

Feb. 27, 2015 (DE) .................. 10 2015 203 546

(51) Int. Cl.
*A61B 6/00* (2006.01)
*A61B 6/03* (2006.01)
(Continued)

(52) U.S. Cl.
CPC .............. *A61B 6/507* (2013.01); *A61B 6/032* (2013.01); *A61B 6/0407* (2013.01);
(Continued)

(58) Field of Classification Search
CPC ... G06T 7/0012; G06T 7/0014; G06T 7/0016; G06T 7/20; G06T 7/269;
(Continued)

(56) References Cited

U.S. PATENT DOCUMENTS 6,005,917 A * 12/1999 Andersson et al. ........ 378/98.12
2009/0086882 A1 4/2009 Grasruck et al. ................ 378/4
(Continued)

FOREIGN PATENT DOCUMENTS

CN 101711683 A 5/2010 ............... A61B 6/03
DE 102007051548 A1 6/2009 ............... A61B 6/03
(Continued)

OTHER PUBLICATIONS

Barfett, Joseph John et al.: "Intra-vascular blood velocity and volumetric flow rate calculated from dynamic 4D CT angiography using a time of flight technique", in: Int J Cardiovasc Imaging 2014, DOI:10.1007/s10554-014-0471-3.
(Continued)

*Primary Examiner* — Andrew W Johns
(74) *Attorney, Agent, or Firm* — Harness, Dickey & Pierce, P.L.C.

(57) ABSTRACT

A method for determining the velocity of a fluid in a volume to be imaged of an examination object with the aid of an imaging method is described. Attenuation values are acquired based upon image data of the volume to be imaged, depending on location and time. A temporally and spatially delineated region is specified based upon the acquired attenuation data, in which the acquired attenuation data behaves approximately linearly. Subsequently, temporal and/or spatial gradients and/or a combination of a temporal and a spatial gradient are determined based upon the attenuation values associated with the temporally and spatially delineated region. Finally, the velocity of the fluid is calculated based upon the determined temporal and/or spatial gradients or from the combination of a temporal and a spatial gradient and from the temporal gradient. A fluid velocity determining device, non-transitory computer readable
(Continued)

medium and a computed tomography system are also described.

23 Claims, 9 Drawing Sheets

(51) Int. Cl.
 A61B 6/04 (2006.01)
 G06T 7/00 (2017.01)
(52) U.S. Cl.
 CPC .......... *A61B 6/0457* (2013.01); *A61B 6/486* (2013.01); *G06T 7/0016* (2013.01); *A61B 6/5205* (2013.01); *G06T 2200/04* (2013.01); *G06T 2207/10081* (2013.01); *G06T 2207/30104* (2013.01)
(58) Field of Classification Search
 CPC .......... G06T 2207/30104; A61B 6/486; A61B 6/507; A61B 6/5205
 See application file for complete search history.

(56) References Cited

U.S. PATENT DOCUMENTS

| | | | |
|---|---|---|---|
| 2009/0124892 A1 | 5/2009 | Bruder et al. | 600/425 |
| 2011/0274333 A1 | 11/2011 | Prevrhal et al. | 382/132 |
| 2013/0172734 A1 | 7/2013 | Hsieh | 600/425 |
| 2015/0043708 A1 | 2/2015 | Allmendinger et al. | A61B 6/032 |

FOREIGN PATENT DOCUMENTS

| | | | |
|---|---|---|---|
| DE | 102013215807 A1 | 2/2015 | A61B 6/03 |
| JP | 2006296707 A | 11/2006 | A61B 6/00 |
| JP | 2007105242 A | 4/2007 | A61B 6/03 |

OTHER PUBLICATIONS

Prevrhal, Sven et al.: "CT Angiographic Measurement of Vascular Blood Flow Velocity by Using Projection Data", in: Radiology 2011; vol. 261, No. 3, pp. 923-929.
German Office Action dated Oct. 15, 2015.

\* cited by examiner

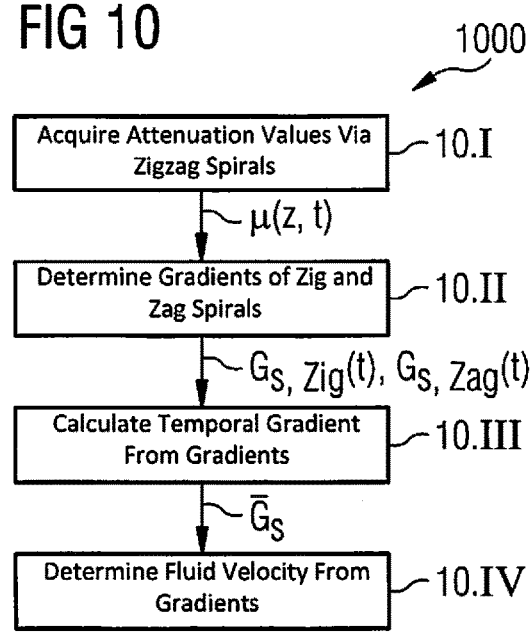
FIG 10
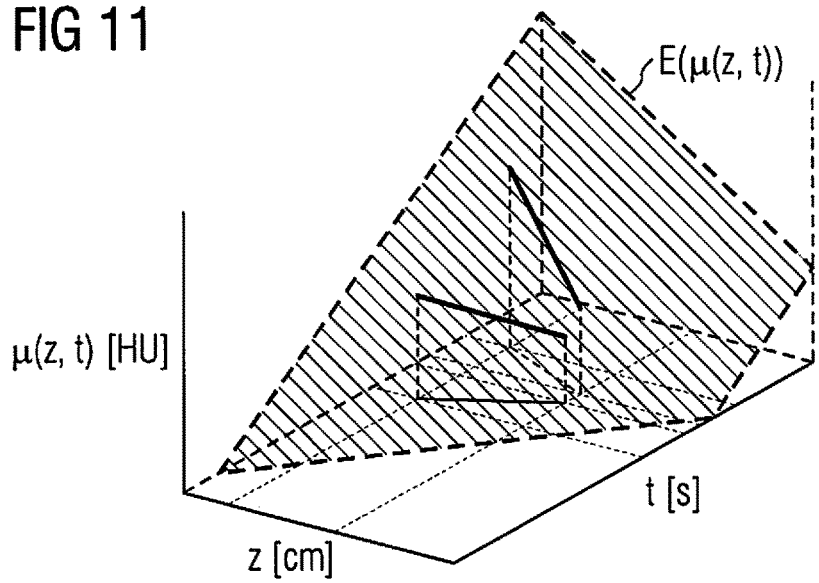
FIG 11
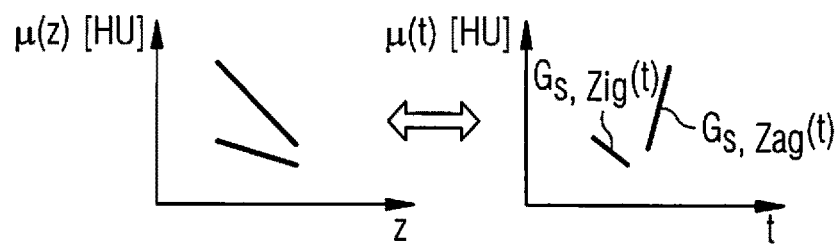

DETERMINING THE VELOCITY OF A FLUID WITH THE AID OF AN IMAGING METHOD

PRIORITY STATEMENT

The present application hereby claims priority under 35 U.S.C. § 119 to German patent application number DE 102015203546.8 filed Feb. 27, 2015, the entire contents of which are hereby incorporated herein by reference.

FIELD

At least one embodiment of the invention generally relates to a method for determining the velocity of a fluid in a volume to be imaged of an examination object with the aid of an imaging method, preferably computed tomography. At least one embodiment of the invention also generally relates to a fluid velocity determining device. At least one embodiment of the invention further generally relates to a computed tomography system.

BACKGROUND

With the aid of modern imaging methods, two or three-dimensional image data is often created which can be used for visualizing an imaged examination object and also for further uses.

Frequently, the imaging methods are based on the detection of X-ray radiation, wherein "projection scan data" is generated. For example, projection scan data can be acquired with the aid of a computed tomography (CT) system. In CT systems, typically a combination of an X-ray source and an oppositely arranged X-ray detector mounted on a gantry run round a measurement space in which the examination object (which in the following is designated "patient" without any restriction of the generality) is situated. The center of rotation (also known as "isocenter") coincides with a "system axis" z. During one or two rotations, the patient is irradiated with X-ray radiation from the X-ray source, wherein projection scan data or X-ray projection data is acquired with the aid of the X-ray detector positioned opposite thereto.

The projection scan data generated is dependent particularly on the construction of the X-ray detector. X-ray detectors typically have a plurality of detector units which are usually arranged in a regular pixel array. The detector units each generate, for X-ray radiation falling on the detector units, a detector signal which is analyzed at particular time points with regard to intensity and spectral distribution of the X-ray radiation in order to draw conclusions about the examination object and to generate projection scan data.

With the aid of CT imaging, for a long time it has "only" been possible to image anatomical structures. Functional imaging via computed tomography was for a long time not possible, however, partially because of an excessive radiation loading on the patient. In the last few years, however, due to technological progress, the possibilities for functional imaging have improved and they have found their way into clinical routine. However, the search for functional measuring variables continues and one of these has been sought after for a particularly long time: the measurement of flow velocity in blood vessels.

In the first place, knowledge of blood flow velocities can help to find and/or characterize pathologies (e.g. stenoses). Secondly, it enables optimization of the acquisition parameters for CT scans supported by contrast medium, for example, angiography scans. The determination of the blood flow velocity is already possible with medical measuring methods such as magnetic resonance tomography (MRT) and ultrasound (US). When determining the blood flow velocity with the aid of magnetic resonance tomography, body tissues can be brought via magnetic fields into a particular electromagnetic state. From the change in magnetization, for example, via the blood flow, the velocity of the blood is determined (using "Magnetic Resonance Velocimetry"). Contrast media are not always needed for this method.

When determining the blood flow rate with the aid of an ultrasonic method, however, the Doppler effect is used, wherein via the frequency shift in the sound waves, it is revealed how high the blood flow velocity is. With this method also, no contrast medium is needed and, in a similar way, there are also optical methods (e.g. with a laser) to measure the blood flow velocity using the Doppler effect.

For CT imaging methods, there are several patented methods for measuring blood flow velocity, as described for example, in the following scientific publications and patent applications: a first method comprises a process wherein from the time offset of the individual projections on the detector, the blood flow velocity during a contrast medium-supported scan is to be determined. This method is described in Prevrhal, S. et al., "CT angiographic measurement of vascular blood flow velocity by using projection data", Radiology 2011; 261: 923-929 and in the patent application US 2011/0274333 A1.

A second method also comprises a process wherein from the time offset of the individual projections on the detector, the blood flow velocity during a contrast medium-supported scan is to be determined. In this method, as in the first method, it is only projection data or sinograms that are used, but not image data. This second method is described in J J Barfett et al., "Intra-vascular blood velocity and volumetric flow rate calculated from dynamic 4D CT angiography using a time of flight technique", Int J Cardiovasc Imaging 2014, DOI:10.1007/s10554-014-0471-3 and in US 2013/0172734 A1.

A third method has essentially the same approach as the first and the second methods, although it is supported on the processing of image data in place of projection data. This third method is described in the patent application US 2009/0086882 A1. In the third method, acquisitions take place parallel to the z-axis at different discrete time points. In this regard, the z-axis should be understood to be the virtual axis, also known as the system axis, about which the scanning system rotates. These acquisitions are carried out as repeated sequence scans with a broad collimation. Therefrom, spatial gradients can be derived at the different acquisition times. Similarly, temporal gradients Gt can also be derived at fixed z-positions.

Furthermore, the acquisition is restricted by the maximum coverage of the detector in the z-direction. The blood flow velocity dz/dt is then calculated from the displacement of the spatial gradients.

SUMMARY

The inventors have recognized that the methods outlined have the following limitations: they only function when the scanning system and the object being investigated do not move relative to one another in the z-direction. This is an essential boundary condition for the conventional method described. This arises therefrom that conventionally a displacement of the gradients in the spatial and temporal direction along the spatial and temporal coordinate axes is included in the calculation of the blood flow velocity and therefore the conventional methods are not usable for scans which correspond to a non-parallel trajectory to the coordinate axes in the space-time coordinate system. The length of the region to be investigated is restricted by the size or the dimensions of the detector in the z-direction.

The acquisition processes of the methods described are restricted to temporally different scans at the same z-position or spatially different scans at the same time points. Scans of this type in which the relative velocity between the examination object and the scanning system in the z-direction has the value zero, can be designated a "sequential scan". In contrast thereto, scans in which the relative velocity between the examination object and the scanning system in the z-direction has a value not equal to zero, are referred to below as "spiral acquisition".

In addition, the accuracy of the blood flow velocity measurement depends on how large the detector is in the z-direction: The smaller the detector is, the poorer is the accuracy. Furthermore, in the methods described, the temporal and spatial resolution is discrete since the detector has a fixed number of detector elements in the z-direction (layers) and has a minimum temporal resolution which depends on the rotary velocity of the gantry. In addition, in the methods outlined, it is often required that the region of the object to be investigated is scanned at least twice. For many CT devices with small detector widths of e.g. 1-2 cm, the methods described above thus cannot be usefully applied. Typically, in the methods described, fluid velocity measurements with satisfactory accuracy are possible only with very wide detectors with widths of, for example, 16 cm.

Accordingly, in an embodiment of the present invention, a method is developed for determining the flow velocity in a body region to be investigated, which is also flexibly usable with conventional CT devices with sufficient accuracy and for different CT image recording types, for example, including with a relative movement between the examination object and the CT detector in the z-direction.

At least one embodiment is directed to a method for determining the velocity of a fluid according; at least one embodiment is directed to a fluid velocity determining device; and at least one embodiment is directed to a computed tomography system.

In the method according to an embodiment of the invention for determining the velocity of a fluid in a volume of an examination object to be imaged with the aid of an imaging method, preferably computed tomography, attenuation values are acquired on the basis of image data of the volume to be imaged, depending on location and time. These attenuation values can be, for example from image data of a contrast medium acquired with the aid of the imaging method, preferably a CT scanning method, the contrast medium flowing after injection through a blood vessel in the volume to be imaged.

A temporally and spatially delineated region in which the acquired attenuation data behaves approximately linearly temporally and spatially is determined and specified on the basis of the attenuation data acquired. For the temporal specification, for example, the temporally linear portions of the contrast medium concentration curve shown in FIG. 2 can be used.

Subsequently, temporal and/or spatial gradients or a combination of temporal and spatial gradients are determined on the basis of the attenuation values associated with the temporally and spatially delineated region. Based on the assumption of the linear properties of the region taken into account when determining the gradients, the gradients are valid for the entire delineated region. On the basis of the temporal and/or spatial gradients determined, the velocity of the fluid is calculated.

The fluid velocity determining device according to an embodiment of the invention has a measurement value determining unit for acquiring attenuation values based on image data of a volume to be imaged of an examination object, depending on place and time. The fluid velocity determining device according to the invention further comprises a region specification unit for specifying a temporally and spatially delineated region on the basis of the acquired attenuation data in which the acquired attenuation data behaves approximately linearly. The fluid velocity determining device according to the invention further comprises a gradient determining unit for determining temporal and/or spatial gradients on the basis of the attenuation values associated with the temporally and spatially delineated region. Finally, the fluid velocity determining device according to the invention also comprises a velocity calculation unit for calculating the velocity of the fluid on the basis of the temporal and/or spatial gradients determined.

The computed tomography system according to an embodiment of the invention has the fluid velocity determining device according to the invention.

The computed tomography system according to an embodiment of the invention also has, for example, a projection data acquisition unit. The projection data acquisition unit comprises an X-ray source and a detector system for acquiring projection scan data of an object. Furthermore, the computed tomography system according to an embodiment of the invention also comprises a reconstruction unit for reconstructing acquired projection scan data and also the fluid velocity determining device according to an embodiment of the invention.

In particular the fluid velocity determining device according to an embodiment of the invention can be part of a user terminal or a control device of a CT system.

A realization largely through software has the advantage that, for example, conventionally used control devices can also be upgraded easily with a software update in order to operate in the manner according to an embodiment of the invention. An embodiment therefore includes a suitable non-transitory computer readible medium with a computer program, which can be loaded directly into a memory storage unit of a control device of a computed tomography system, and including program portions in order to carry out all the steps of the method according to an embodiment of the invention when the program is executed in the control device. A computer program product or computer readible medium of this type can possibly comprise, apart from the computer program, additional constituent parts such as documentation and/or additional components including hardware components such as hardware keys (dongles etc.) for use of the software.

A non-transitory computer-readable medium, for example a memory stick, a hard disk or another transportable or firmly installed data carrier on which the program portions of the computer program which can be read in by a computer unit of the control device are stored, can serve for transport to the control device and/or for storage on or in the control device. For this purpose, the computer unit can have one or more cooperating microprocessors or the like.

The dependent claims and the following description contain particularly advantageous embodiments and developments of the invention. Herein particularly, the claims of one claim category can also be further developed similarly to the dependent claims of another claim category. In addition, within the context of the invention, the various features of different example embodiments and claims can also be combined to new example embodiments.

BRIEF DESCRIPTION OF THE DRAWINGS

The invention will now be described in greater detail making reference to example embodiments as illustrated in the accompanying drawings, in which:

FIG. 10 is a flow diagram to illustrate the method for determining the velocity of a fluid according to a fifth example embodiment of the invention, FIG. 11 is a graphical representation to illustrate the method for determining the velocity of a fluid according to a fifth example embodiment of the invention.

DETAILED DESCRIPTION OF THE EXAMPLE EMBODIMENTS

Figure 1:
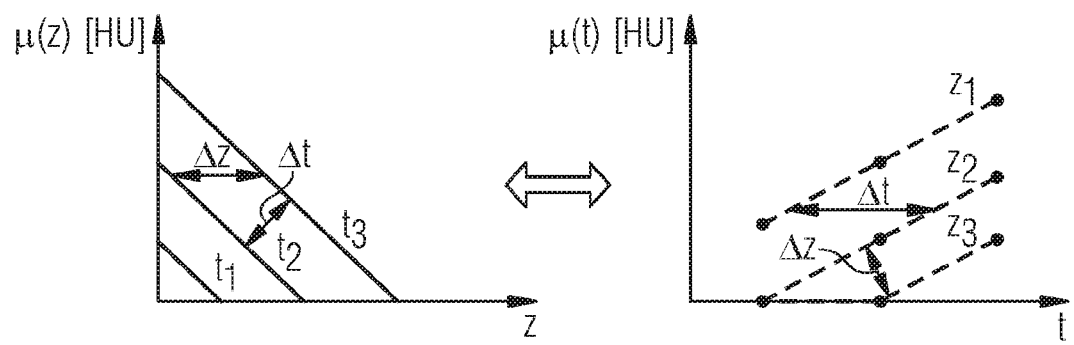
FIG. 1 is a schematic representation of a conventional approach for determining a blood flow velocity.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Further, although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In the method according to an embodiment of the invention for determining the velocity of a fluid in a volume of an examination object to be imaged with the aid of an imaging method, preferably computed tomography, attenuation values are acquired on the basis of image data of the volume to be imaged, depending on location and time. These attenuation values can be, for example from image data of a contrast medium acquired with the aid of the imaging method, preferably a CT scanning method, the contrast medium flowing after injection through a blood vessel in the volume to be imaged.

A temporally and spatially delineated region in which the acquired attenuation data behaves approximately linearly temporally and spatially is determined and specified on the basis of the attenuation data acquired. For the temporal specification, for example, the temporally linear portions of the contrast medium concentration curve shown in FIG. 2 can be used.

Subsequently, temporal and/or spatial gradients or a combination of temporal and spatial gradients are determined on the basis of the attenuation values associated with the temporally and spatially delineated region. Based on the assumption of the linear properties of the region taken into account when determining the gradients, the gradients are valid for the entire delineated region. On the basis of the temporal and/or spatial gradients determined, the velocity of the fluid is calculated.

The method according to an embodiment of the invention has the following advantages in comparison with the conventional first to third methods discussed in the introductory part of the description: the length of the region to be investigated is no longer restricted by the size of the detector in the z-direction, since movement no longer necessarily has to take place parallel to the temporal axis or the spatial axis. This applies for example, for spiral acquisitions in which the relative velocity between the examination object and the scanning system in the z-direction has a value not equal to zero.

The accuracy of the blood flow velocity measurement no longer depends on the size of the detector in the z-direction since the length of the scan in the z-direction (and thus the accuracy), for example, of a spiral acquisition can be freely selected.

Both the temporal and the spatial resolution are freely selectable with, for example, a spiral acquisition, for example, via the pitch, slice thickness and increment of the images.

It is no longer absolutely necessary to scan the region to be investigated at least twice if a useful scan of the linear temporally and spatially delineated region is achieved with variable speed, for example, with a spiral at variable velocity.

The fluid velocity determining device according to an embodiment of the invention has a measurement value determining unit for acquiring attenuation values based on image data of a volume to be imaged of an examination object, depending on place and time. The fluid velocity determining device according to the invention further comprises a region specification unit for specifying a temporally and spatially delineated region on the basis of the acquired attenuation data in which the acquired attenuation data behaves approximately linearly. The fluid velocity determining device according to the invention further comprises a gradient determining unit for determining temporal and/or spatial gradients on the basis of the attenuation values associated with the temporally and spatially delineated region. Finally, the fluid velocity determining device according to the invention also comprises a velocity calculation unit for calculating the velocity of the fluid on the basis of the temporal and/or spatial gradients determined.

The computed tomography system according to an embodiment of the invention has the fluid velocity determining device according to the invention.

The computed tomography system according to an embodiment of the invention also has, for example, a projection data acquisition unit. The projection data acquisition unit comprises an X-ray source and a detector system for acquiring projection scan data of an object. Furthermore, the computed tomography system according to an embodiment of the invention also comprises a reconstruction unit for reconstructing acquired projection scan data and also the fluid velocity determining device according to an embodiment of the invention.

The essential components of the fluid velocity determining device according to the invention can be configured mainly in the form of software components. This particularly relates to the region specification unit, the gradient determining unit and the velocity calculation unit. In principle, however, these components can also be realized in part, especially if particularly fast calculations are to be performed, in the form of software-supported hardware, for example, FPGAs or the like. If, for example, what is concerned is merely a transfer of data from other software components, the required interfaces can also be configured as software interfaces. However, they can also be configured as interfaces constructed with hardware, which are controlled via suitable software.

In particular the fluid velocity determining device according to an embodiment of the invention can be part of a user terminal or a control device of a CT system.

A realization largely through software has the advantage that, for example, conventionally used control devices can also be upgraded easily with a software update in order to operate in the manner according to an embodiment of the invention. An embodiment therefore includes a suitable non-transitory computer readible medium with a computer program, which can be loaded directly into a memory storage unit of a control device of a computed tomography system, and including program portions in order to carry out all the steps of the method according to an embodiment of the invention when the program is executed in the control device. A computer program product or computer readible medium of this type can possibly comprise, apart from the computer program, additional constituent parts such as documentation and/or additional components including hardware components such as hardware keys (dongles etc.) for use of the software.

A non-transitory computer-readable medium, for example a memory stick, a hard disk or another transportable or firmly installed data carrier on which the program portions of the computer program which can be read in by a computer unit of the control device are stored, can serve for transport unit to the control device and/or for storage on or in the control device. For this purpose, the computer unit can have one or more cooperating microprocessors or the like.

The dependent claims and the following description contain particularly advantageous embodiments and developments of the invention. Herein particularly, the claims of one claim category can also be further developed similarly to the dependent claims of another claim category. In addition, within the context of the invention, the various features of different example embodiments and claims can also be combined to new example embodiments.

In one embodiment of the method according to the invention for determining the velocity of a fluid, the fluid in question is blood which flows through a blood vessel in the volume to be imaged. For example, a contrast medium is injected into the blood and is made visible with the aid of an imaging method.

Advantageously, in the temporally and spatially delineated region, a plane of attenuation values is determined depending on location and time on the basis of the acquired attenuation values. The spatial and temporal gradients result from the parameters defining the plane, wherein the advantage exists that, in contrast to conventional methods, the trajectory of the acquisition of the attenuation values in space and time is no longer subject to any restrictions since the gradients are not directly determined from the acquired attenuation values, but from the plane generated thereby. For example, the attenuation values must no longer be acquired parallel to the temporal and spatial axis. The expression "plane" should be not be understood in this context as restricted to a two-dimensional space-time diagram. If the calculation of the fluid velocity is based, for example, on a plurality of spatial dimensions, the expression "plane" should be understood to mean that the same spatial gradient (in this case, a vector) can be associated with each attenuation value in the delineated region.

In a preferred embodiment of the method according to the invention, the plane is determined with the aid of a curve-fitting method on the basis of the acquired attenuation values depending on location and time. With the aid of averaging, for example with a method which is based on the principle of least squares, statistical errors can be corrected when scan data is incorporated.

Preferably, in the method according to an embodiment of the invention, the temporal gradient and the spatial gradient of the determined plane are determined as the temporal gradient and the spatial gradient. These should be understood to be the slope values of the plane in the z-direction and in the time direction.

In a particularly practicable variant of the method according to an embodiment of the invention, the temporal gradient is determined from the slope of the line of intersection between the plane and the $\mu$-z-plane formed by the axis of the attenuation values and the z-axis and the spatial gradient is determined from the slope of the line of intersection between the plane and the $\mu$-t-plane formed by the axis of the attenuation values and the time axis.

Particularly preferably, the velocity of a fluid is determined on the basis of the product of the determined temporal gradient and the determined spatial gradient. In this variant, the spatial gradient should be understood to be the reciprocal value of the slope of the line of intersection between the plane and the μ-t-plane formed by the axis of the attenuation values and the time axis.

If the spatial gradient is defined, as conventionally, as the slope of the line of intersection between the plane and the μ-t-plane formed by the axis of the attenuation values, then the velocity of the fluid is obtained on the basis of the quotient of the determined temporal gradient and the determined spatial gradient.

In a variant of the method according to an embodiment of the invention which is particularly advantageously to be applied, the velocity of the fluid in the case of a relative movement between the examination object and the scanning system is determined on the basis of a relation similar to the Doppler equation. This relation exists between a combination of a temporal gradient and a spatial gradient and an additionally determined temporal gradient. In this variant, an image recording is carried out, for example, with a moving patient table. If, as usual for CT scans, the detector is rotated during the image recording, then a "spiral scan" is the result. Similarly to the Doppler equation, in this special variant, the simple product relation used for determining the fluid velocity is modified such that in addition to the temporal gradient, a combination of temporal and spatial gradients is now also made use of for calculating the fluid velocity.

The velocity of the fluid can then be determined in this special variant according to the following formula:

$$v_{fld} = \frac{\pm v_{tb}}{\frac{G_s(t)}{G_t(t)} - 1}, \tag{1}$$

where $v_{fld}$ is the velocity of the fluid, $v_{tb}$ is the velocity of the moving examination object, $G_s(t)$ is a projection of a combination of temporal and spatial gradient in the μ-t-plane which is formed by the time axis and the axis of the attenuation values ($\mu(z,t)$) and $G_t(t)$ is a mean temporal gradient.

In a particularly advantageous embodiment of the method according to an embodiment of the invention, the determined temporal gradient can be determined on the basis of a bolus tracking scan.

The bolus-tracking scan can be used, for example, with a broad collimation. In this case, the plane for determining the gradients and thus the fluid velocity can even be determined from the bolus-tracking scan alone.

In the context of this variant, the attenuation values acquired on the basis of the bolus-tracking scan can serve to determine the velocity of the fluid and, on the basis of the determined velocity, a pitch value of the image recording of the moving examination object can be selected such that the attenuation values acquired during the image recording of the moving examination object are approximately constant. Subsequently, in a following imaging process, control of the scanning system preferably takes place with the determined pitch value. This variant has the advantage that in the actual imaging, the contrast values for the same materials are very uniform, which can be highly advantageous in the diagnosis based on the acquired image data.

Alternatively, the movement direction and/or the velocity of the moving examination object can also be adjusted during the image recording of the moving examination object.

In a special variant of the method according to an embodiment of the invention, the image recording with a relative movement between the examination object and the scanning system comprises a change in the relative velocity between the examination object and the scanning system and a change in the collimation of the image recording. A recording of this type is also designated a VVS scan, where VVS stands for spiral acquisition with a variable velocity.

In the variants described which can also be treated with the aid of relations using formulae similar to the Doppler equations, the scanning system and the examination object may move relative to one another in the z-direction (which means that "spiral acquisitions in particular are permitted"). In these cases, the fluid velocity can be particularly easily calculated with the aid of relations similar to the Doppler equations.

Advantageously, the fluid velocity determining device according to an embodiment of the invention has a plane-determining unit for determining a plane of attenuation values depending on location and time on the basis of the acquired attenuation values. If a plane is initially determined on the basis of the determined attenuation values, then the spatial and temporal gradients to be determined for the calculation of the fluid velocity can be determined independently of the trajectory of the CT image recording. Furthermore, via the intermediate step of determining a plane, an error correction of local statistical errors can also be realized for the CT image recording.

All these embodiments offer very many possibilities for effectively carrying out blood flow velocity measurements with imaging devices, for example, CT devices. Use of the Doppler principle for contrast medium-supported CT scans is not in the least obvious since the scanning principle has nothing to do with optical or acoustic waves.

FIG. 1 shows a schematic representation of a conventional approach for determining a blood flow velocity. The approach illustrated in FIG. 1 corresponds to the third method described above. The HU values or attenuation values $\mu(z)$ given in left graphical representation in FIG. 1 are acquired at different discrete time points $t_1$, $t_2$, $t_3$ parallel to the z-axis with the aid of a CT system. These acquisitions are carried out as repeated sequence scans with a broad collimation. From the function values determined or from the gradient of the corresponding graphs, spatial gradients can be derived at the different acquisition times.

In the right graph of FIG. 1, HU values are shown as a function of time. The attenuation values $\mu(t)$, also known as HU values are normally given in the units HU (for Hounsfield units). These HU values were acquired at different discrete positions $z_1$, $z_2$, $z_3$ in the z-direction.

From the slopes of the graphs obtained, temporal gradients are derived at fixed z-positions.

From the spatial and temporal displacements $\Delta z$ and $\Delta t$ of the acquired spatial and temporal gradients (as found from one of the two partial graphs), the blood flow velocity $v_{fld}$ can be calculated as follows:

$$v_{fld} = \frac{\Delta z}{\Delta t}. \tag{2}$$

Figure 2:
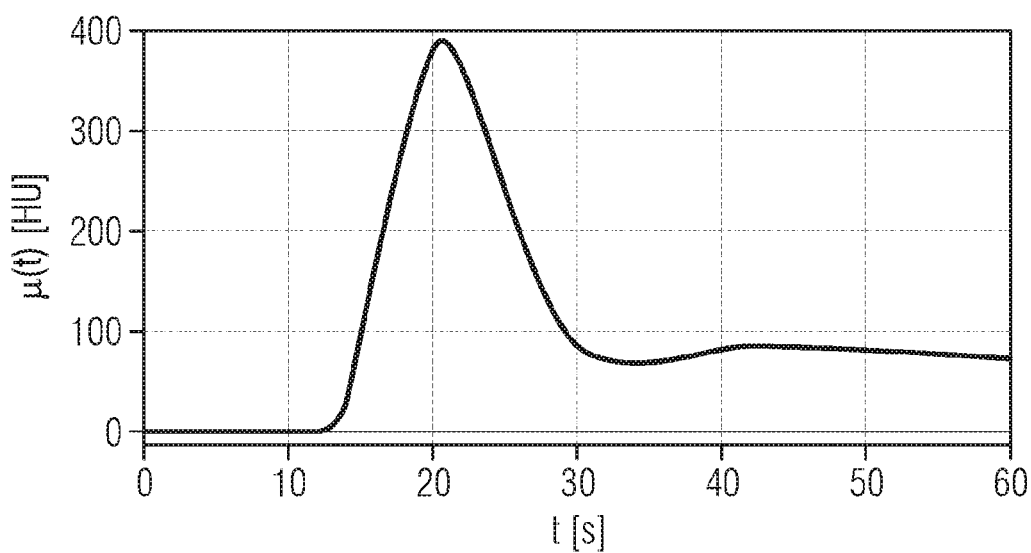
FIG. 2 is the variation over time of a contrast medium curve.

FIG. 2 shows the temporal variation of the contrast medium concentration in a blood vessel on injection of a contrast medium into a vessel system. The graph has been created on the basis of attenuation values $\mu(t)$ measured in the blood vessel with the aid of a CT system. The attenuation values μ(t) acquired were measured at a constant z-position. For the sake of simplicity, it has been made a pre-condition that the blood vessel is oriented in the z-direction and has a fixed diameter. It is also assumed that no contrast medium can emerge through the vessel wall.

The temporal progress of the curve of the HU values shown in FIG. 2 can be interpreted as follows: the heart pumps the blood through the vessel system at a constant cardiac output and an average velocity $v_{fld}$. Following the start of the injection of a contrast medium, the contrast medium concentration in the blood vessel initially rises at least for the duration of the injection of the contrast medium. This means that, at a fixed z-position, over the course of time, the HU value initially increases and then decreases again, depending on the injection protocol, as illustrated for example, in the example shown in FIG. 2, wherein the rising flank of the contrast medium curve or, more precisely, the curve of the HU values can be regarded as the temporal gradient $G_t(t)$ of the contrast medium. At the same time, a spatial gradient $G_z(z)$ also arises in the blood vessel, since the z-positions which are closer to the heart "see" the higher HU values sooner than the lower z-positions. This spatial gradient $G_z(z)$ can be detected in patients.

It is apparent from the contrast medium curve that the aforementioned temporal gradients $G_z(t)$ have a constant value in particular time intervals, for example, between t=12 s and t=20 s. In the region also of the falling curve of HU values between t=22 s and t=28 s, the temporal gradients $G_t(t)$ have an essentially constant value. Similarly, it can be shown that in the z-direction, at least for a particular region and a particular time interval, a spatial gradient $G_t(z)$ with a constant value is to be expected. This applies under the assumption that the cardiac output is constant.

The blood flow velocity $v_{fld}$ can now be determined directly from these gradients $G_t(t)$, $G_z(z)$ through simple multiplication of the temporal gradient $G_t(t)$ with the spatial gradient $G_z(z)$, wherein in this notation, the spatial gradient $G_z(z)$ should be understood as the reciprocal of the slope of the lines of intersection between the plane and the μ-t-plane formed by the axis of the attenuation values and the time axis:

$$V_{fld}=G_z(z)[m/HU]*G_t(t)[HU/s]. \qquad (3)$$

This formula bears a similarity to the known formula $$c=\lambda*f, \qquad (4)$$

which gives, inter alia for sound waves, the relationship between the speed of sound c, the wavelength λ and the frequency f. In this analogy, the wavelength λ corresponds to the spatial gradient $G_z(z)$ in equation (3), the frequency f corresponds in this analogy to the temporal gradient $G_t(t)$ in equation (3) and the speed of sound c corresponds to the blood flow velocity $v_{fld}$ in equation (3).

Figure 3:
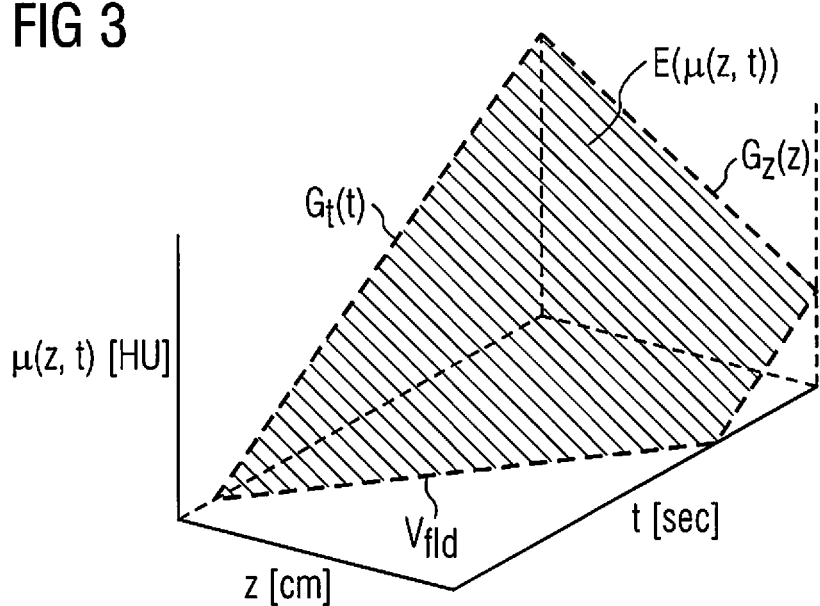
FIG. 3 is a graphical representation to illustrate the linear behavior of the contrast medium concentration in a blood vessel.

If the slopes corresponding to the two gradients $G_z(z)$ and $G_t(t)$ are represented in one graph, then the result is the presentation of FIG. 3. From the two gradients $G_z(z)$ and $G_t(t)$, or more accurately, from straight lines having slopes corresponding to the two gradients $G_z(z)$ and $G_t(t)$, a plane E(μ(z,t)) is stretched out which corresponds to the distribution of the attenuation values μ(z,t) acquired during an image recording as a contrast medium is administered. Expressed precisely, the slope of the lines of intersection, denoted in FIG. 3 with the reference sign $G_z(z)$, between the plane E(μ(z,t)) and the μ-t-plane formed by the axis of the attenuation values and the time axis corresponds to the reciprocal value of the gradient $G_z(z)$ according to the definition used for equation (3). This distribution is herein a plane since, on the basis of the graph in FIG. 2, the assumption has been made that at least for a particular time t and a particular space z, the temporal and spatial gradients are linear. The fluid velocity $v_{fld}$, the graph of which runs diagonally in the z-t plane in the graphical representation of FIG. 3, is given by equation (3).

Figure 4:
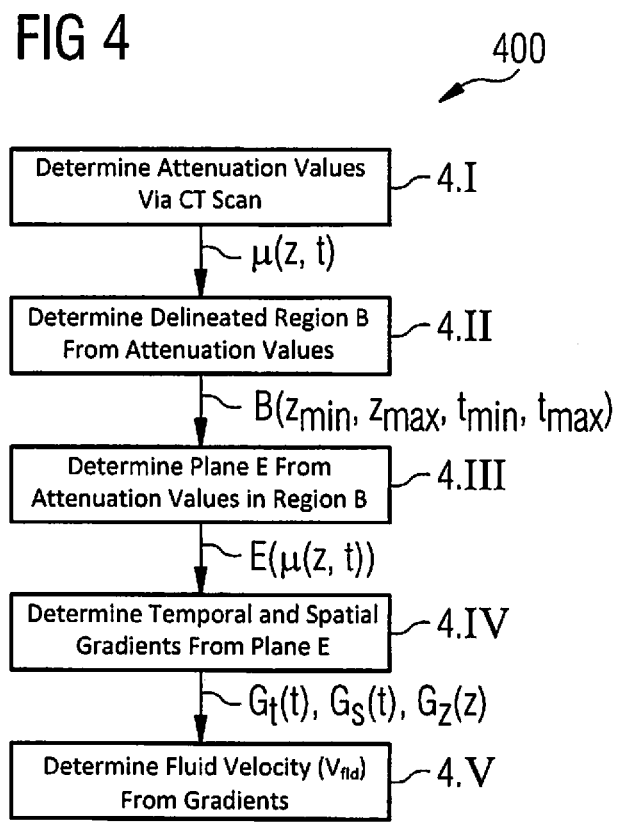
FIG. 4 is a flow diagram to illustrate the method for determining the velocity of a fluid according to a first example embodiment of the invention.

FIG. 4 shows a flow diagram to illustrate a method 400 for determining the velocity of a fluid according to a first example embodiment of the invention. As previously mentioned, an underlying concept of the invention lies therein that the gradients $G_z(z)$ and $G_t(t)$ shown in FIG. 3 are determined by the plane E(μ(z,t)).

In step 4.I, initially attenuation values μ(z,t) are determined with the aid of a CT scan. In contrast to the conventional process according to the third method, however, the choice of the spatial and temporal coordinates in which the attenuation values μ(z,t) are determined is open within certain limits, i.e. in the linear regions as shown in FIG. 2 or in regions with a constant gradient. As will become clear in the example embodiments set out below, this freedom in the recording of the attenuation values μ(z,t) opens the possibility of using very different types of CT imaging methods with different trajectories in the scan data space defined by the coordinates z and t, which are not usable in the conventional velocity determining methods.

In step 4.II, a temporally and spatially delineated region B ($z_{min}$, $z_{max}$, $t_{min}$, $t_{max}$) is stipulated on the basis of the acquired attenuation data (μ(z,t)), in which region the acquired attenuation data (μ(z,t)) behaves approximately linearly. I.e. minimum values $z_{min}$, $t_{min}$ and maximum values $z_{max}$, $t_{max}$ are stipulated for time and location within which the acquired attenuation data (μ(z,t)) behaves approximately linearly. Mostly, there is a limitation in the z-direction caused by the scan length which is selected by a radiologist and this depends on the body region to be examined. In principle, the length must not be restricted in the z-direction. Theoretically, scanning could be performed "endlessly" in the z-direction for as long as the assumption applies that the gradients remain constant and linear over such a long time.

In step 4.III, a plane E (μ(z,t)) is determined on the basis of the attenuation values (μ(z,t)) acquired during the image recording in the delineated region B ($z_{min}$, $z_{max}$, $t_{min}$, tmax). For example, on the basis of these values, a plane equation can be determined. Since the measurement values or the acquired attenuation values μ(z,t) do not lie exactly on the plane due to expected statistical measuring errors and the inaccuracies resulting therefrom, it is useful to define the plane depending on the acquired attenuation values μ(z,t) with the aid of a mathematical curve-fitting method. A method of this type is, for example, the orthogonal linear regression in 3-D space.

Subsequently, in step 4.IV, on the basis of the acquired plane E, gradients $G_t(t)$, $G_z(z)$ are determined. These gradients or their values correspond, for the temporal gradient $G_t(t)$, the slope of the lines of intersection of the plane E and a plane formed from the t-axis and the μ-axis, also known as the μ-t-plane, and for the spatial gradient $G_z(z)$, the slope of the lines of intersection of the plane E and a plane formed from the z-axis and the μ-axis, also known as the μ-z-plane, as indicated in FIG. 3. Following determination of the lines of intersection, the values of the gradients $G_t(t)$, $G_z(z)$ are found from the slope of these lines of intersection.

In step 4.V, the fluid velocity $v_{fld}$ is determined on the basis of equation (3), i.e. a product is formed from the temporal and spatial gradients.

Figure 5:
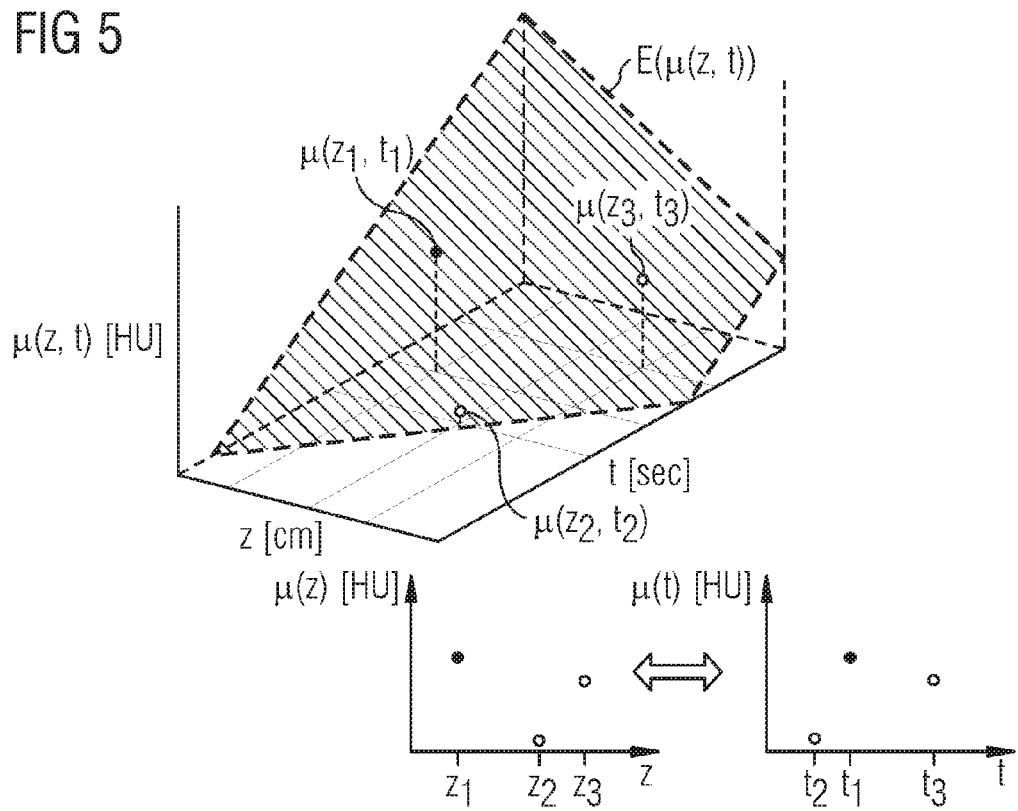
FIG. 5 is a graphical representation to illustrate the method for determining the velocity of a fluid according to a first example embodiment of the invention.

In FIG. 5, the determination of the plane E, by way of example, on the basis of attenuation values μ($z_1,t_1$), μ($z_2,t_2$), μ($z_3,t_3$) acquired is shown in a graphical representation. The attenuation values acquired can be associated with corresponding points in the graph, on the basis of which a plane E is determined. In this variant, the points in the graph corresponding to the acquired attenuation values μ($z_1,t_1$), μ($z_2,t_2$), μ($z_3,t_3$) are three non-colinear points. With the representation of the plane in the graphical representation, the projections of the points associated with the attenuation values μ($z_1,t_1$), μ($z_2,t_2$), μ($z_3,t_3$) onto the plane comprising the t-axis and the μ-axis, hereinafter referred to as the μ-t-plane, and onto the plane comprising the z-axis and the μ-axis, hereinafter referred to as the μ-z-plane, are also shown. It is evident therefrom that due to the lack of co-linearity of the points associated with the acquired attenuation values μ($z_1,t_1$), μ($z_2,t_2$), μ($z_3,t_3$) in the graphical representation, from the projections shown below the graph in the μ-t-plane and the μ-z-plane, the spatial and temporal gradients $G_z(z)$, $G_t(t)$ sought cannot be derived directly, as would be a pre-condition for a successful use of the conventional methods for fluid velocity determination, in particular the third method as described in detail in the introduction to the description.

As previously mentioned, the spatial and temporal gradients can be determined according to the invention for the temporal gradient $G_t(t)$ from the slope of the lines of intersection of the plane E and a plane formed from the t-axis and the μ-axis, also named the μ-t-plane, and for the spatial gradient $G_z(z)$ from the slope of the lines of intersection of the plane E and a plane formed from the z-axis and the μ-axis, also named the μ-z-plane. The fluid velocity $v_{fld}$ as per equation (3) is found from the gradients $G_t(t)$ and $G_z(z)$, i.e. by multiplication of the two gradients $G_t(t)$ and $G_z(z)$.

In order to carry out the recording of the attenuation values, three sequence scans with the narrowest collimation would be carried out at three different z-positions and three different time points. The gradients $G_t(t)$ and $G_z(z)$ can also be determined simply by way of an algebraic derivation.

Figure 6:
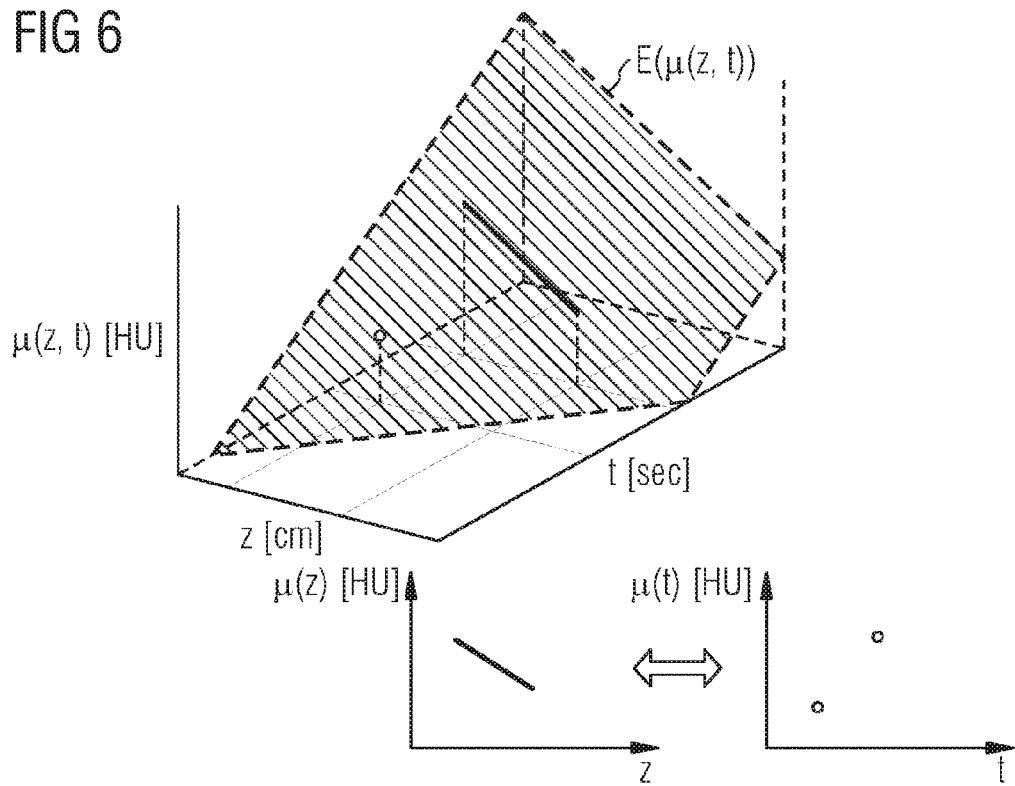
FIG. 6 is a graphical representation to illustrate the method for determining the velocity of a fluid according to a second example embodiment of the invention.

In FIG. 6, the determination of the plane E is shown, by way of example, on the basis of attenuation values acquired in a graphical representation for a method for determining the fluid velocity in a volume to be imaged of an examination object with the aid of an imaging method, according to a second example embodiment. Herein, the relevant representation showing the acquired attenuation values forms a straight line in the graphical representation and a point not lying thereon. This variant corresponds to a CT scan with two sequence acquisitions, collimated once broadly and once narrowly. This variant is more advantageous for the patient in comparison with conventional methods, since a smaller radiation dose is applied with the acquisition using the narrow collimation. However, herein also, the maximum scan in the z-direction is restricted by the dimensions of the detector.

FIG. 6 shows, under the representation of the plane E, the projections of the graphical representation onto the μ-t-plane from the t-axis and the μ-axis and onto the μ-z-plane from the z-axis and the μ-axis. Here also, it is apparent that in this case, the determination of the fluid velocity according to the conventional third method as per equation (1) without the plane E would encounter difficulties since the temporal and spatial displacement of the gradients is not discernible from the projections. From the plane E determined, however, according to the invention, the gradients $G_z(z)$ and $G_t(t)$ being sought, can be determined and from the gradients Gt(t) and Gz(z) determined, subsequently, the fluid velocity $v_{fld}$ can be calculated using equation (3). In this special case, the spatial and temporal gradients $G_z(z)$, $G_t(t)$ can alternatively be derived without determining a plane E, simply from the measurements or the attenuation values μ(z,t) acquired thereby, since these have been acquired parallel to the z-axis and the t-axis.

Other variants of the embodiments shown relate to the acquisition of attenuation values, the representation of which in the graphical representation results in two mutually intersecting straight lines or two truly parallel straight lines. Essentially, for the accuracy when determining the fluid velocity, the more scans that exist for the plane E (e.g. due to repeated measurements of attenuation values at different time points or at other z-positions), the better is the estimate of the area of the plane E and thus also that of the gradients $G_t(t)$, $G_z(z)$.

If a blood vessel does not lie parallel to the z-axis, the measured blood flow velocity $v_{zfld}$ along the z-axis can easily be converted into the actual velocity in the vessel:

$$V_{fld}=v_{zfld}/\cos(\theta), \quad (5)$$

where θ is the angle between the vessel and the z-axis.

Figure 7:
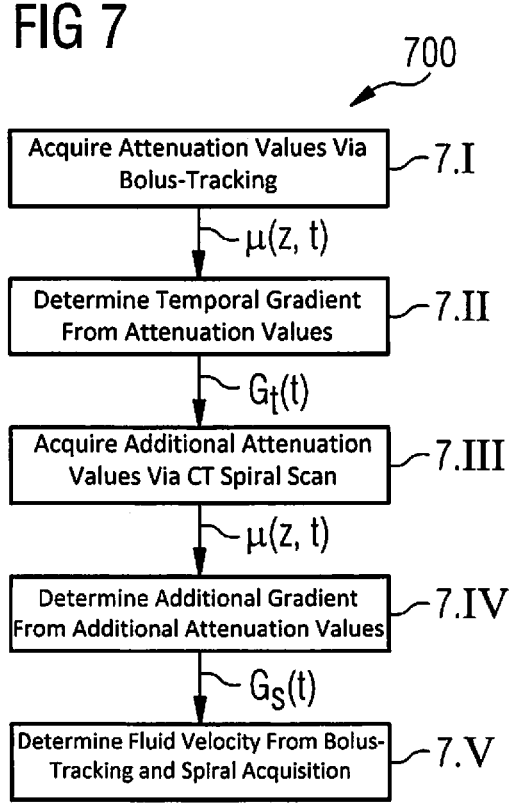
FIG. 7 is a flow diagram to illustrate the method for determining the velocity of a fluid according to a third example embodiment of the invention.

FIG. 7 shows a flow diagram to illustrate a method 700 for determining the velocity of a fluid according to a third example embodiment of the invention. In step 7.I, the attenuation values μ($t_1$), μ($t_2$), μ($t_3$) for this example embodiment are acquired with the aid of "bolus-tracking". Herein, the concentration of an injected contrast medium is measured as a function of time. In this case, attenuation values are acquired with the bolus-tracking signal in step 7.I, from which, in step 7.II, the temporal gradient $G_t(t)$ is determined directly. This is possible under the condition that the rise in the contrast medium concentration curve remains constant. This assumption is justified over the duration of the injection and for as long as the blood has not yet recirculated in the patient.

Subsequently, in step 7.III, additional attenuation values are acquired with the aid of a CT spiral scan. A CT spiral scan is a scan method in which the examination object is moved relative to the detector of the imaging system. An example of this type of acquisition of the attenuation values is shown in the graphical representation of FIG. 8. This variant is very practical since it exploits clinical practice which is already common. On the basis of the spiral acquisition which covers the entire z-region in the example shown in FIG. 8, in step 7.IV, an additional temporal gradient $G_s(t)$ is determined. The additional temporal gradient $G_s(t)$ is herein the projection of the straight lines, corresponding to the spiral acquisition, of the attenuation values acquired during the spiral acquisition in the upper graphical representation of FIG. 8 onto the μ-t-plane.

In step 7.V, the fluid velocity $v_{fld}$ is determined from the bolus-tracking signal and the spiral acquisition. Put more precisely, in order to determine the fluid velocity $v_{fld}$, the gradients $G_t(t)$ and Gs(t) determined in steps 7.II and 7.IV are used. For this purpose, the known Doppler equations for equation (4), i.e. as used for sound waves, are utilized. For a stationary sound source Q with a moving observer O, the following applies:

$$f_O=f_Q(1+v/c), \quad (6)$$

where $f_O$ is the frequency of the observer O, $f_Q$ is the frequency of the source Q, c is the (sound/wave) velocity and v is the velocity of the observer (negative if moving away from the source). For application to equation (3), that is, the equation for determining the fluid velocity $v_{fld}$ from temporal and spatial gradients $G_t(t)$, $G_z(z)$ which were obtained with the aid of the acquisition of image data using a CT system, a relation similar to the Doppler relation of equation (6) applies:

$$G_s(t) = G_t(t)(1 + v_{tb}/v_{fld}), \qquad (7)$$

where $G_s(t)$ is the projection of a combination $G_s(z,t)$ of the temporal and the spatial gradient on the μ-t-plane, where $G_t(t)$ is the temporal gradient of the heart, $v_{fld}$ is the blood flow velocity and $v_{tb}$ is the table velocity. The table velocity $v_{tb}$ is given, for example, by the pitch, the rotation time and the detector width or the collimation during the CT recording.

The blood flow velocity is then given by rewriting equation (7) as:

$$v_{fld} = \frac{\pm v_{tb}}{\left(\frac{G_s(t)}{G_t(t)} - 1\right)}. \qquad (1)$$

This relation was mentioned above in the brief description of the invention. Herein, $v_{tb} < 0$ applies when moving away from the heart, that is, in the flow direction. This method and the calculation of the fluid velocity described using an analogous system to the Doppler equations was previously carried out successfully with a dynamic phantom.

Figure 8:
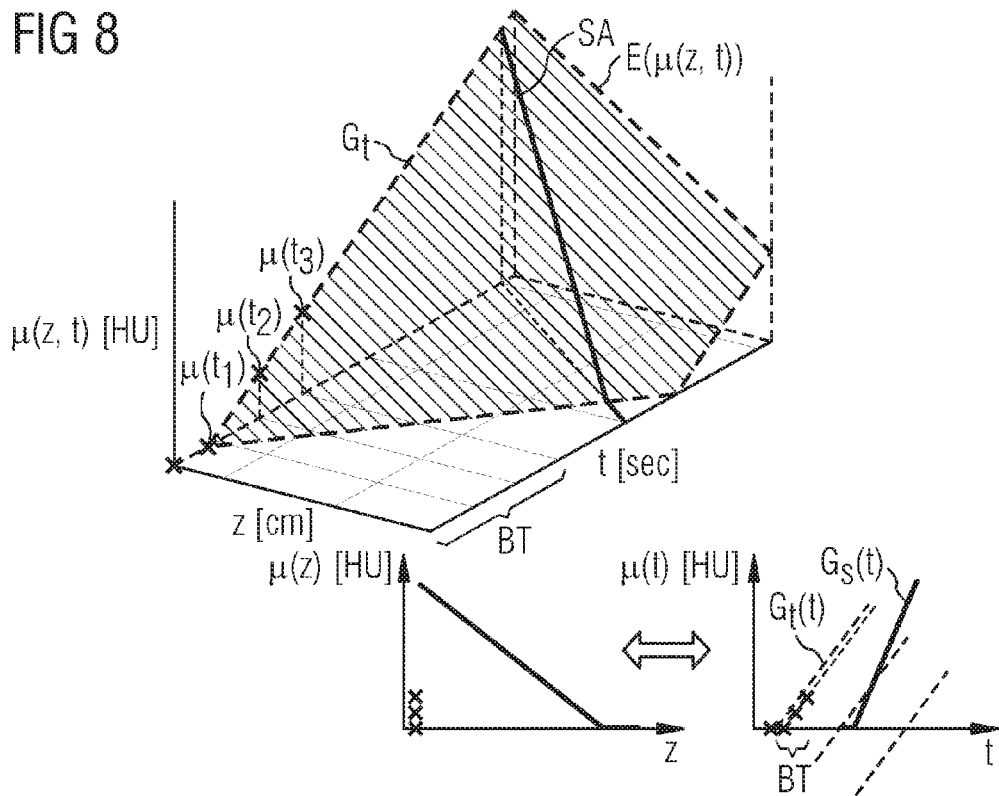
FIG. 8 is a graphical representation to illustrate the method for determining the velocity of a fluid according to a third example embodiment of the invention.

A graphical representation is shown in FIG. 8 in which the method shown in FIG. 7 is illustrated with the aid of a three-dimensional representation of the attenuation values μ(z,t) acquired and projections in the μ-t-plane and the μ-z-plane. As can be seen from the graphical representation, the temporal gradient $G_t(t)$ in the reference frame at rest is given directly by the slope of the graph of the attenuation values μ($t_1$), μ($t_2$), μ($t_3$), which were acquired during bolus tracking BT.

As shown by the projection in the μ-z-plane, the projection of the straight lines of the spiral scan SA in the μ-z-plane does not give the slope of the spatial gradient $G_z(z)$. Rather, the gradient $G_s(z,t)$ representing the slope of the straight line of the spiral scan SA is a combination of the temporal and the spatial gradient. However, from the projection of the straight lines of the spiral scan in the μ-t-plane, a second temporal gradient $G_s(t)$ results, from which together with the temporal gradient $G_t(t)$, the fluid velocity $v_{fld}$ according to equation (1) can be calculated. Alternatively, in this variant also, a plane E can be determined which represents the acquired attenuation values or is approximated thereby and from this, the gradients $G_t(t)$ and $G_z(z)$ can be determined.

Figure 9:
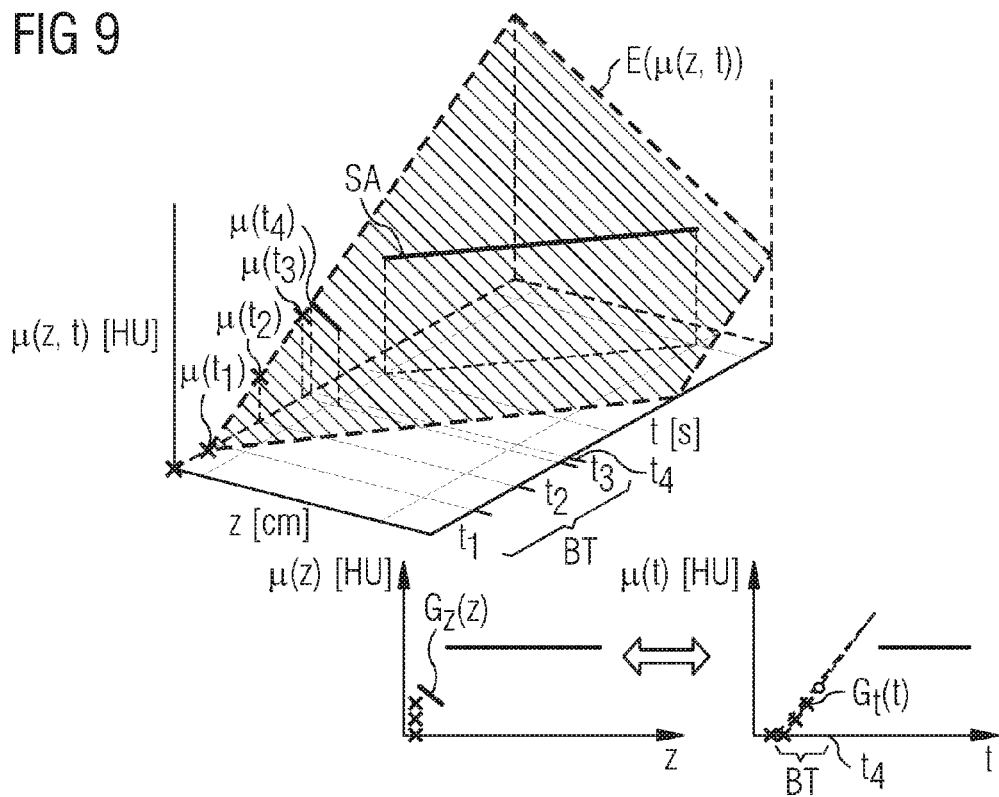
FIG. 9 is a graphical representation to illustrate the method for determining the velocity of a fluid according to a fourth example embodiment of the invention.

FIG. 9 shows an interesting variation, comprising a bolus-tracking scan BT and a subsequent spiral acquisition SA. Herein, the bolus-tracking scan BT is extended by a time point $t_4$, although now with a broader collimation, which can be recognized by the linear distribution extending in the z-direction of the attenuation values μ($t_4$) acquired at the time point $t_4$ in addition to the attenuation values μ($t_1$), μ($t_2$), μ($t_3$) acquired at the time points $t_1$, $t_2$, $t_3$. The reason for this lies therein that with the aid of the attenuation values μ($t_1$), μ($t_2$), μ($t_3$), μ($t_4$) acquired in the bolus-tracking scan, the blood flow velocity $v_{fld}$ is actually already known and, for example, the pitch value of the spiral acquisition can be adjusted in order to ensure a homogeneous enhancement or constant attenuation values μ(z,t) during the spiral acquisition. The constant attenuation values ensure a constant contrast in the CT imaging of a patient under examination, which may be required for making a correct diagnosis on the basis of the image recording.

FIG. 10 shows a flow diagram which illustrates a method for determining the fluid velocity according to a fifth example embodiment. Herein, two zigzag spirals are used in the acquisition of the attenuation values. In this regard, a graphical representation is again shown in FIG. 11 in which the method shown in FIG. 10 is illustrated with the aid of a three-dimensional representation of the attenuation values μ(z,t) acquired and projections in the μ-t-plane and the μ-z-plane. As shown in the projection in the μ-z-plane, the projection of the zigzag movement of the spiral scan in these planes results in two straight lines with different slopes.

In step 10.I, initially the scanning of a relatively large region along the z-axis takes place via repeated spiral scans which alternate in their scan direction. Two of these "sweeps" (zig and zag) are also sufficient to be able to determine the blood flow velocity $v_{fld}$. Subsequently, in step 10.II, the gradients $G_{S,Zig}(t)$ and $G_{s,Zag}(t)$ are determined which correspond to the slopes of the temporal projections shown in FIG. 11, i.e. the projections in the μ-t-plane.

In step 10.III, use is made of the peculiarity that in the zig-zag mode, the table velocity $v_{tb}$ is the same size in both the sweeps, but in opposite directions. On this basis, in step 10.III, the temporal gradient Gt is calculated:

$$G_t(t) = \overline{G_S} = \frac{G_{S,Zig}(t) + G_{S,Zag}(t)}{2}. \qquad (8)$$

From the two measured gradients $G_{S,Zig}(t)$ and $G_{s,Zag}(t)$ of the zig-spiral acquisition and the zag-spiral acquisition, therefore, a mean value which corresponds to the temporal gradient $G_t(t)$ can be calculated.

From equations 1 and 8, in step 10.IV, the fluid velocity $v_{fld}$ is calculated:

$$v_{fld} = \frac{\pm v_{tb}}{\left(\frac{G_s(t)}{G_t(t)} - 1\right)}, \qquad (9)$$

where $G_S(t)$ corresponds either to the gradient of the zig-spiral or the zag-spiral and the table velocity $v_{tb}$ is given the relevant sign. Alternatively, from the two measured gradients $G_{S,Zig}(z,t)$ and $G_{s,Zag}(z,t)$ of the zig-spiral acquisition and the zag-spiral acquisition which represent, in this case, a combination of temporal and spatial gradients, a mean spatial and a mean temporal gradient $G_z(z)$, $G_t(t)$ could be determined and, via equation (3), the velocity $v_{fld}$ determined. As a further alternative, direct fitting of a plane E to the measured HU values and subsequent determination of spatial and temporal gradients $G_z(z)$, $G_t(t)$ representing the slope of the plane in the z-direction and the t-direction is possible.

Figure 12:
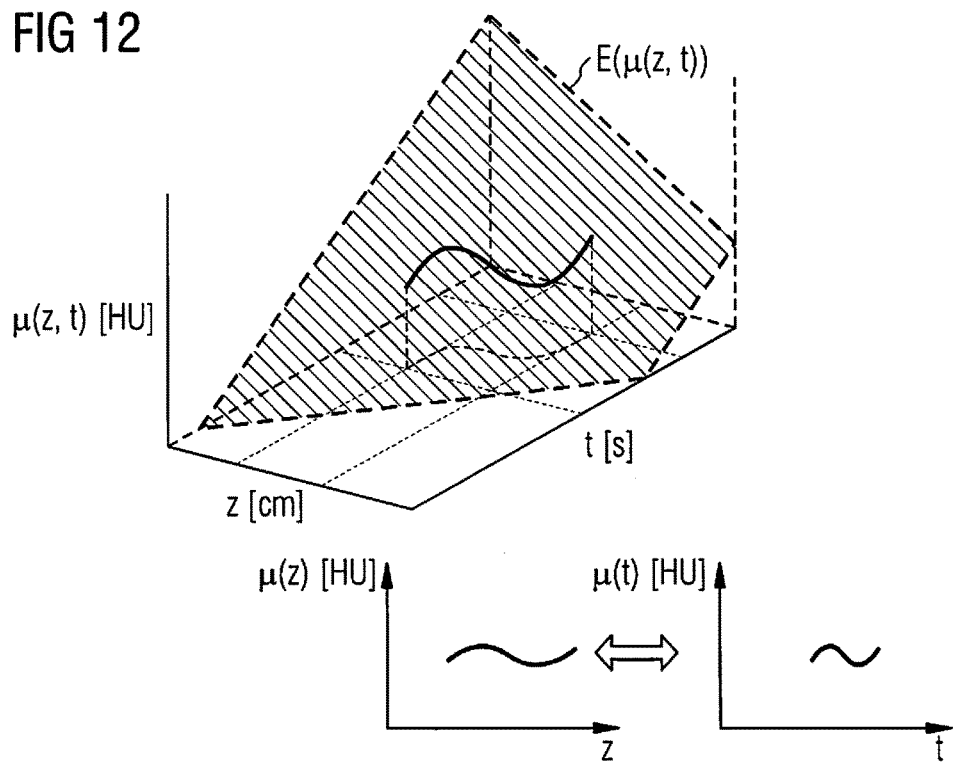
FIG. 12 is a graphical representation to illustrate the method for determining the velocity of a fluid according to a sixth example embodiment of the invention.

FIG. 12 shows a sixth example embodiment of the method according to the invention for determining a fluid velocity, wherein only one spiral acquisition is carried out, this being known under the Siemens name of "Variable Velocity Spiral" (VVS). This type of spiral acquisition enables, given a constant pitch, a simultaneous adjustment of the collimation and the table velocity. With this VVS, theoretically a single acquisition would be sufficient to be able to determine the blood flow velocity. For the determination of the blood flow velocity $v_{fld}$, the possibility still exists of "fitting" a plane E to the measured HU values or of using the Doppler equations (see equations (6), (7), (1)).

In the latter case, the following general approach would have to be taken:

$$G_S(t) = G_t(t) \cdot \left(1 - \frac{\vec{v} \cdot \vec{e}_{QO}}{v_{fld}}\right), \qquad (10)$$

where $\vec{e}_{QO}$ is the unit vector for describing the direction from the source Q to the observer O which, in the general case, can be time-dependent, exactly like the velocity vector $\vec{v}$ which corresponds to the table velocity. Furthermore, the variables $G_s(t)$ and $G_r(t)$ are defined in a similar way to equation (7). In general, the Doppler equations apply only if the contrast medium enrichment increases or decreases monotonically, that is only in the rising or falling flank of the contrast medium curve, as shown in FIG. 2.

The approach with fitting of a plane to the measured attenuation values μ(z,t) can naturally also be refined if, for example, on the basis of a prediction of the contrast medium concentration, the precise shape of the contrast medium curve is known and a more precise description has a surface. In the application, gradients in space and time have been addressed, wherein in particular the partial temporal derivative and the partial derivative in the direction of the z-axis of the attenuation values μ(z,t) were meant.

The actual example embodiments were described on the basis of the blood flow velocity in one direction. However, the invention can be used equally for two-dimensional or three-dimensional fluid velocities. The minimum requirement for scanning or acquiring the attenuation values would then be n+2 non-colinear points, where n is the number of spatial dimensions of the flow velocity.

In order to be less sensitive to image noise, in the case of a direct determination of individual temporal and spatial gradients, linear fits should be performed on the scanned gradients. It can possibly also be useful to be restricted to part of the scanned gradients when determining the fluid velocity $v_{fld}$, for example, if the patient diameter or the angle of the blood vessel changes severely along the z-axis.

It has been described in detail how the blood flow velocity or in general the fluid velocity $v_{fld}$ can be determined. However, other variables can also be (indirectly) derived therefrom, for example, the pressure which prevails in a blood vessel under examination.

Figure 13:
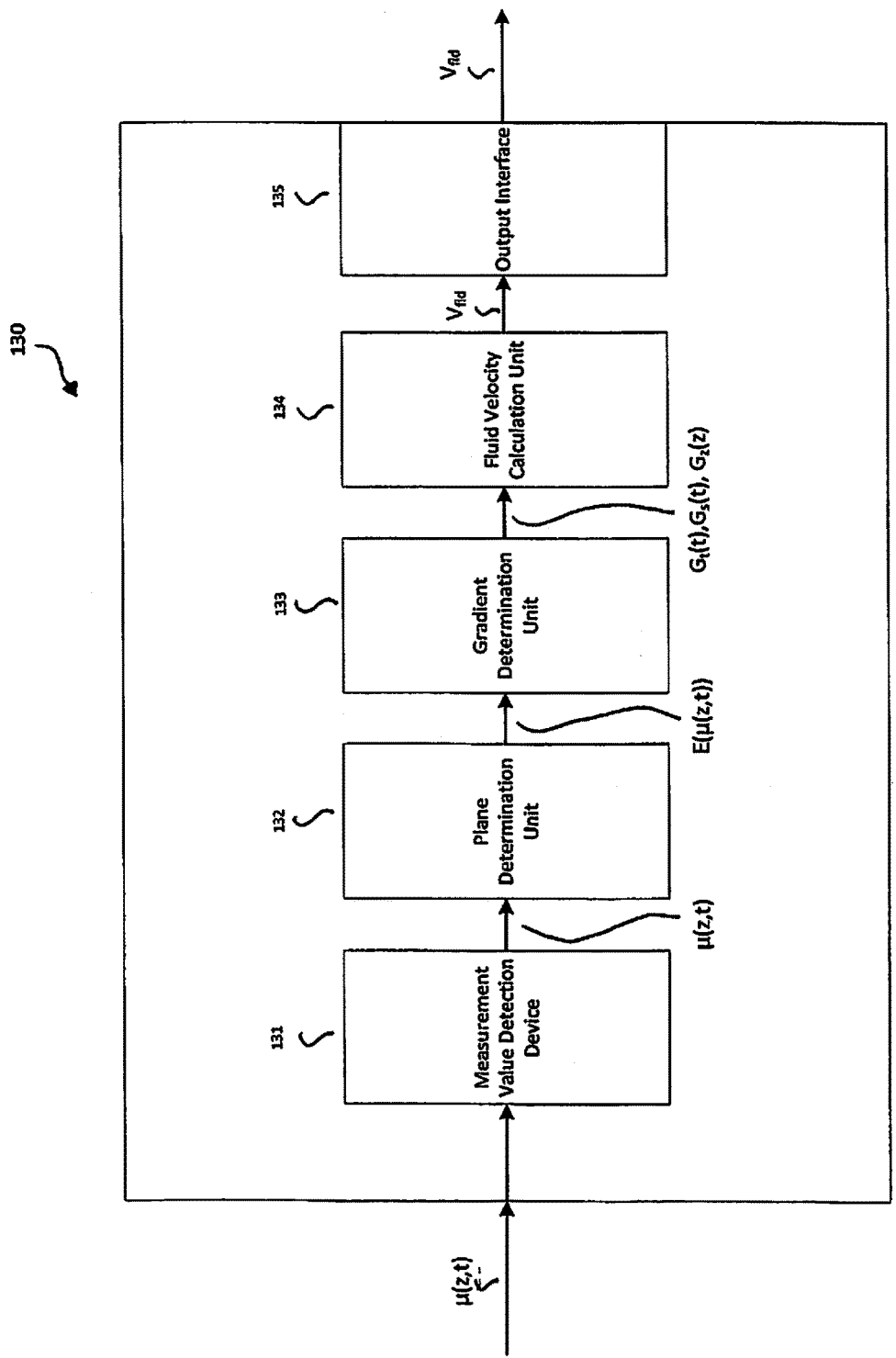
FIG. 13 is a block diagram to illustrate a fluid velocity determining device according to an example embodiment of the invention.

In FIG. 13, a fluid velocity determining device 130 is illustrated. The fluid velocity determining device 130 can be, for example, part of a control device of a CT system 1, such as that shown in FIG. 14. The fluid velocity determining device 130 comprises a measurement value detection device 131 for detecting attenuation values μ(z,t) on the basis of image data BD of a volume VOL to be imaged of an examination object P. The attenuation values μ(z,t) acquired are transferred to a plane determination unit 132 which determines a plane E of attenuation values μ on the basis of the attenuation values μ(z,t). The data determined for the plane E, for example, a plane equation, is transferred to a gradient determining unit 133 which determines, for example, temporal and/or spatial gradients $G_r(t)$, $G_S(t)$, $G_z(t)$ on the basis of attenuation values μ associated with the plane E. The temporal and/or spatial gradients $G_r(t)$, $G_S(t)$, $G_z(z)$ are subsequently transferred to a fluid velocity calculation unit 134 which calculates the velocity $v_{fld}$ of the fluid on the basis of the temporal and/or spatial gradients $G_r(t)$, $G_S(t)$, $G_z(z)$ determined, as described above. The information relating to the fluid velocity $v_{fld}$ determined is subsequently passed on via an output interface 135 to other units such as, for example, a memory store unit or a terminal.

Figure 14:
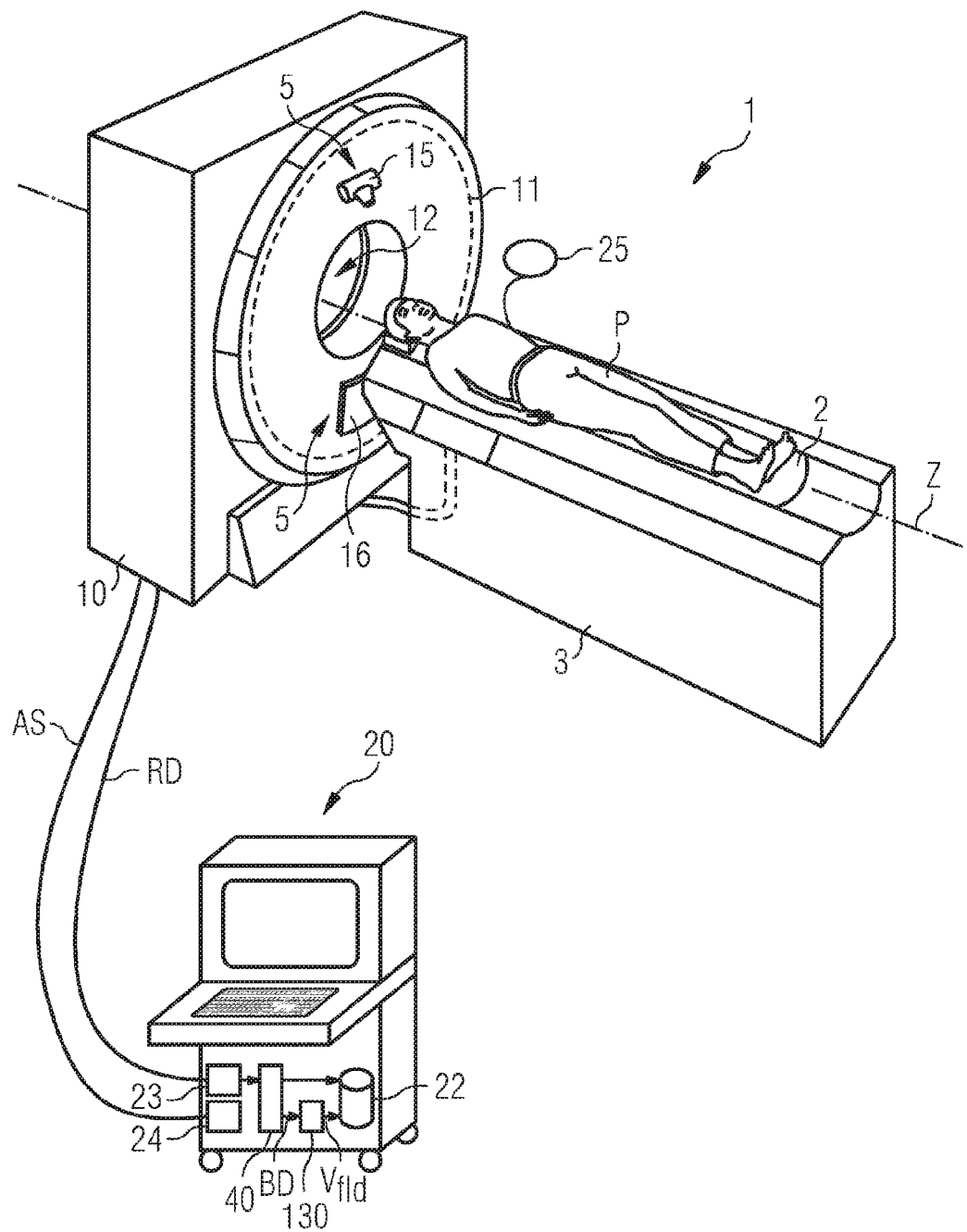
FIG. 14 is a schematic representation of a computed tomography system according to an example embodiment of the invention.

FIG. 14 shows a computed tomography system 1 which comprises the fluid velocity determining device 130 shown in FIG. 13. The CT system 1 substantially consists therein of a conventional scanner 10 in which a projection data acquisition unit 5 with a detector 16 and an X-ray source 15 arranged opposite the detector 16 circulates on a gantry 11 about a measurement space 12. Situated in front of the scanner 10 is a patient positioning device 3 or patient table 3, the upper part 2 of which can be displaced relative to the scanner 10 with a patient P situated thereon in order to move the patient P through the measurement space 12 relative to the detector system 16. The scanner 10 and the patient table 3 are controlled by a control device 20 from which acquisition control signals AS are emitted via a conventional control interface 24 in order to control the entire system in the conventional manner according to pre-determined scan protocols. In the event of a spiral acquisition (as described in relation to FIGS. 7 to 12), a movement of the patient P along the z-direction which corresponds to the system axis z longitudinally through the measurement space 12 and the simultaneous circulation of the X-ray source 15, a helical path of the X-ray source 15 relative to the patient P results during the scan. The detector 16 always runs in parallel with and opposite to the X-ray source 15 in order to acquire projection scan data RD which is used for reconstructing volume image data and/or slice image data. Similarly, a sequential scanning method as described in relation to FIGS. 4 to 6 can be carried out wherein a fixed position is approached in the z-direction and then, during a rotation, a partial rotation or a plurality of rotations at the z-position in question, the required projection scan data RD is acquired in order to reconstruct a sectional image at this z-position or in order to reconstruct image data from the projection data of a plurality of z-positions. The method according to the invention is, in principle, usable in other CT systems, for example, with a plurality of X-ray sources and/or detectors and/or with a detector forming a complete ring. For example, the method according to the invention can also be used on a system with a static patient table and a gantry moving in the z-direction ("sliding gantry").

The projection scan data RD (referred to hereinafter as raw data RD) acquired from the detector 16 is transferred via a raw data interface 23 to the control device 20. This raw data is then further processed, possibly following a suitable pre-processing (e.g. filtration and/or beam-hardening correction) in an image reconstruction device 40 which in this example embodiment is realized in the control device 20 in the form of software on a processor. This image reconstruction device 40 reconstructs image data BD on the basis of the raw data RD with the aid of a reconstruction method. As the reconstruction method, for example, a reconstruction method based on the filtered back-projection can be used.

The reconstructed image data is subsequently transferred to a fluid velocity determining device 130 as shown in detail in FIG. 13. The fluid velocity determining device 130 determines, on the basis of the determined image data BD or the attenuation values μ(z,t) correlated thereto, the fluid velocity $v_{fld}$.

The fluid velocity $v_{fld}$ determined by the fluid velocity determining device 130 and the acquired image data BD is then placed in a memory store 22 of the control device 20 and/or output in the usual manner on the screen of the control device 20. They can also be fed via an interface (not shown in FIG. 14) into a network connected to the computed tomography system 1, for example a radiological information system (RIS), and placed in a mass storage device accessible there or output as images on printers or filming stations connected thereto. The data can thus be further processed in any desired manner and then stored or output.

Additionally, in FIG. 14, a contrast medium injecting device 25 is shown with which the patient P is injected with contrast medium, the behavior of which, for example, in a heart vessel is recorded as images with the aid of the computed tomography system 1.

The components of the image reconstruction device 40 and of the fluid velocity determining device 130 can be realized mainly or entirely in the form of software elements on a suitable processor. In particular, the interfaces between these components can also be realized purely with software. It is required only that possibilities exist for access to suitable memory store regions in which the data can suitably be placed in intermediate storage and called up again at any time and updated.

The actual example embodiments of the invention have been described in relation to the use of CT acquisitions wherein the unit of attenuation is Hounsfield units (HU). Naturally, this approach can also be used with other arrangements. This applies, for example, for the measurement of material properties other than X-ray attenuation, for example, the temperature or optical density.

Finally, it should again be noted that the methods and devices described are merely preferred embodiments of the invention and that the invention can also be varied by a person skilled in the art without departing from the field of the invention as defined by the claims. Thus, the method and the fluid velocity determining device have been described primarily on the basis of a computed tomography system for recording medical image data. However, the invention is not restricted to use in computed tomography, nor to use in the medical domain, rather the invention can in principle be used with other imaging systems and also for the recording images for other purposes. For the sake of completeness, it should also be mentioned that the use of the indefinite article "a" or "an" does not preclude the relevant feature from also being present plurally. Similarly, the expression "unit" does not preclude this consisting of a plurality of components which may possibly also be spatially distributed.

The aforementioned description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods. Further, elements and/or features of different example embodiments may be combined with each other and/or substituted for each other within the scope of this disclosure and appended claims.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Further, at least one embodiment of the invention relates to a non-transitory computer-readable storage medium comprising electronically readable control information stored thereon, configured in such that when the storage medium is used in a controller of a magnetic resonance device, at least one embodiment of the method is carried out.

Even further, any of the aforementioned methods may be embodied in the form of a program. The program may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for determining a velocity of a fluid in a volume to be imaged of an examination object with aid of an imaging method, the method comprising:
acquiring attenuation values based upon image data of the volume to be imaged, depending on location and time;
specifying a temporally and spatially delineated region based upon acquired attenuation data in which the acquired attenuation values behave approximately linearly;
determining at least one of temporal gradients, spatial gradients and a combination of temporal and spatial gradients based upon the attenuation values associated with the temporally and spatially delineated region; and determining the velocity of the fluid based upon the determined at least one of temporal and spatial gradients of the determined at least one of temporal gradients, spatial gradients and combination of temporal and spatial gradients or from the combination of temporal and spatial gradients and from the temporal gradients of the determined at least one of temporal gradients, spatial gradients and combination of temporal and spatial gradients.

2. The method of claim 1, wherein the fluid is blood which flows through a blood vessel in the volume to be imaged.

3. The method of claim 2, wherein in the temporally and spatially delineated region, a plane of attenuation values is determined depending on location and time based upon the acquired attenuation values.

4. The method of claim 1, wherein in the temporally and spatially delineated region, a plane of attenuation values is determined depending on location and time based upon the acquired attenuation values.

5. The method of claim 4, wherein the plane of attenuation values is determined with aid of a curve-fitting method based upon the acquired attenuation values depending on location and time.

6. The method of claim 4, wherein as the temporal gradient and as the spatial gradient, the temporal gradient and the spatial gradient of the determined plane of attenuation values are determined.

7. The method of claim 4, wherein a temporal gradient, of the determined at least one of temporal gradients, spatial gradients and a combination of temporal and spatial gradients, is determined from a slope of lines of intersection between the plane of attenuation values and a μ-z-plane formed by an axis of the attenuation values and a z-axis and wherein a spatial gradient, of the determined at least one of temporal gradients, spatial gradients and a combination of temporal and spatial gradients, is determined from a slope of lines of intersection between the plane and a μ-t-plane formed by an axis of the attenuation values and a time axis.

8. The method of claim 1, wherein the velocity of the fluid is determined based upon a product of a determined temporal gradient and a determined spatial gradient of the determined at least one of temporal gradients, spatial gradients and a combination of temporal and spatial gradients.

9. The method of claim 1, wherein the velocity of the fluid, in a case of a relative movement between the examination object and measurement space, is determined based upon a relation similar to a Doppler equation between a combination of a temporal gradient and a spatial gradient and a temporal gradient.

10. The method of claim 9, wherein the velocity ($v_{fld}$) of the fluid is determined according to the following equation:

$$v_{fld} = \frac{\pm v_{tb}}{\frac{G_s(t)}{G_t(t)} - 1},$$

where $v_{fld}$ is the velocity of the fluid, $v_{tb}$ is the velocity of the examination object when moving, (P), $G_s(t)$ is a projection of a combination ($G_s(z,t)$) of temporal and spatial gradient in a μ-t-plane formed by a time axis and an axis of the attenuation values and $G_t(t)$ is a temporal gradient.

11. The method of claim 10, wherein a bolus-tracking scan is used with a broad collimation.

12. The method of claim 11, wherein the examination object is a moving examination object and wherein, based upon the attenuation values acquired with aid of the bolus-tracking scan, a velocity of the fluid is determined and based upon the velocity determined, a pitch value of an image recording of the moving examination object is selected such that the attenuation values acquired during the image recording of the moving examination object are approximately constant.

13. The method of claim 12, wherein, during a subsequent imaging, control of a scanning system is carried out with the selected pitch value.

14. The method of claim 10, wherein the temporal gradient $G_t(t)$ is determined based upon a bolus-tracking scan.

15. The method of claim 9, wherein the temporal gradient is determined based upon a bolus-tracking scan.

16. The method of claim 9, wherein a bolus-tracking scan is used with a broad collimation.

17. The method of claim 1, wherein the examination object is a moving examination object and wherein, during an image recording of the moving examination object, at least one of a movement direction and a velocity of the moving examination object are changed.

18. The method of claim 1, the examination object is a moving examination object and wherein an image recording of the moving examination object comprises a change of a velocity of the moving examination object and a change of a collimation of the image recording.

19. A non-transitory computer readable medium comprising a computer program, loadable directly into a memory store of a control device of a computed tomography system, including program portions to carry out the method of claim 1 when the computer program is executed in the control device of the computed tomography system.

20. A non-transitory computer-readable medium including program portions, readable and executable by a computer unit, to carry out the method of claim 1 when the program portions are carried out by the computer unit.

21. The method of claim 1, wherein the imaging method is computed tomography.

22. A fluid velocity determining device, comprising:
a first memory storing computer-readable instructions; and
one or more processors configured to execute the computer-readable instructions to
acquire attenuation values based upon image data of a volume of an examination object to be imaged, depending on location and time,
specify a temporally and spatially delineated region based upon acquired attenuation data in which the acquired attenuation values behaves approximately linearly,
determine at least one of temporal gradients, spatial gradients and a combination of temporal and spatial gradients based upon the attenuation values associated with the temporally and spatially delineated region, and
determine a velocity of the fluid based upon the determined at least one of temporal and spatial gradients of the determined at least one of temporal gradients, spatial gradients and combination of temporal and spatial gradients or from the combination of a temporal and a spatial gradient and from the temporal gradient of the determined at least one of temporal gradients, spatial gradients and combination of temporal and spatial gradients.

23. A computed tomography system, comprising the fluid velocity determining device of claim 22.

\* \* \* \* \*